United States Patent
Kitaoka et al.

(10) Patent No.: US 8,982,200 B2
(45) Date of Patent: Mar. 17, 2015

(54) INTRAORAL CAMERA WITH LIGHT COLLECTING FACES THAT DEFLECT LIGHT CLOSE TO AN IMAGING WINDOW

(75) Inventors: Yasuhisa Kitaoka, Tokushima (JP); Toshiaki Ueta, Ehime (JP); Yoshiki Ishikawa, Ehime (JP); Mitsuhiro Iwata, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 887 days.

(21) Appl. No.: 13/130,152

(22) PCT Filed: Sep. 13, 2010

(86) PCT No.: PCT/JP2010/005574
§ 371 (c)(1),
(2), (4) Date: May 19, 2011

(87) PCT Pub. No.: WO2011/052129
PCT Pub. Date: May 5, 2011

(65) Prior Publication Data
US 2011/0221878 A1    Sep. 15, 2011

(30) Foreign Application Priority Data

Oct. 27, 2009  (JP) ................................. 2009-246166
Nov. 12, 2009  (JP) ................................. 2009-258597

(51) Int. Cl.
*H04N 7/18*  (2006.01)
*A61B 1/06*  (2006.01)
*A61B 1/247*  (2006.01)

(52) U.S. Cl.
CPC .............. *A61B 1/0676* (2013.01); *A61B 1/247* (2013.01); *A61B 1/0623* (2013.01); *A61B 1/0684* (2013.01)

USPC .................................. 348/66; 433/29; 348/61

(58) Field of Classification Search
CPC .............. H04N 7/18; A62B 1/04; A61C 1/00; A61C 3/00
USPC .......................................................... 348/66
See application file for complete search history.

(56) References Cited

U.S. PATENT DOCUMENTS 4,781,448 A * 11/1988 Chatenever et al. .......... 359/701
5,016,098 A    5/1991  Cooper et al.
(Continued)

FOREIGN PATENT DOCUMENTS

CA    2 178 240    12/1996
EP    0 326 497    8/1989
(Continued)

OTHER PUBLICATIONS

Supplementary European Search Report issued May 6, 2013 in corresponding European Application No. EP 10 82 5821.

*Primary Examiner* — Jessica M Prince
(74) *Attorney, Agent, or Firm* — Wenderoth, Lind & Ponack, L.L.P.

(57) ABSTRACT

An intraoral camera including a main body case, an intraoral insertion component mounted on the front side of the main body case, an imaging window provided to the intraoral insertion component, and an imaging device that is optically linked to the imaging window and is disposed inside the main body case or inside the intraoral insertion component. Illumination elements are disposed at portions of an outer peripheral wall face that are substantially opposite each other in the horizontal direction. These illumination elements are inclined toward the outside of the imaging window in the center of the imaging window, and the outer peripheral wall face that is substantially opposite these illumination elements in the vertical direction is constituted as a light collecting face that is inclined toward the outside of the imaging window in the center of the imaging window.

13 Claims, 10 Drawing Sheets

(56) References Cited

U.S. PATENT DOCUMENTS

| | | | |
|---|---|---|---|
| 5,702,249 A | 12/1997 | Cooper | |
| 5,745,165 A * | 4/1998 | Atsuta et al. | 348/65 |
| 5,865,725 A | 2/1999 | Arai et al. | |
| 6,181,369 B1 | 1/2001 | Ooshima et al. | |
| 6,190,309 B1 | 2/2001 | Ooshima et al. | |
| 7,010,223 B2 | 3/2006 | Thoms | |
| 7,570,984 B2 * | 8/2009 | Katsuda et al. | 600/407 |
| 2001/0000672 A1 | 5/2001 | Ooshima et al. | |
| 2003/0107652 A1 * | 6/2003 | Williams | 348/207.99 |
| 2004/0156626 A1 | 8/2004 | Thoms | |
| 2005/0043586 A1 | 2/2005 | Suzushima | |
| 2006/0015012 A1 * | 1/2006 | Sato | 600/118 |
| 2007/0093691 A1 * | 4/2007 | Kobayashi | 600/180 |
| 2008/0086160 A1 * | 4/2008 | Mastri et al. | 606/185 |

FOREIGN PATENT DOCUMENTS

| | | |
|---|---|---|
| EP | 1 604 606 | 12/2005 |
| GB | 2 301 975 | 12/1996 |
| JP | 41-4670 | 3/1966 |
| JP | 8-332170 | 12/1996 |
| JP | 10-33461 | 2/1998 |
| JP | 10-258021 | 9/1998 |
| JP | 10-272095 | 10/1998 |
| JP | 11-113836 | 4/1999 |
| JP | 11-505732 | 5/1999 |
| JP | 11-192207 | 7/1999 |
| JP | 11-253398 | 9/1999 |
| JP | 2004-65623 | 3/2004 |
| JP | 2004-275542 | 10/2004 |
| JP | 2004-532083 | 10/2004 |
| JP | 2005-52165 | 3/2005 |
| JP | 2005-80734 | 3/2005 |
| JP | 2005-152569 | 6/2005 |
| JP | 2006-192027 | 7/2006 |
| JP | 2007-282804 | 11/2007 |

* cited by examiner

INTRAORAL CAMERA WITH LIGHT COLLECTING FACES THAT DEFLECT LIGHT CLOSE TO AN IMAGING WINDOW

TECHNICAL FIELD

The present invention relates to an intraoral camera for capturing an image of a tooth, for example.

BACKGROUND ART

A conventional intraoral camera was constituted as follows.

A conventional intraoral camera comprised a main body case, an intraoral insertion component mounted on the front side of this main body case, an imaging window provided to this intraoral insertion component, and an imaging device that was optically linked to this imaging window and was disposed inside the main body case or inside the intraoral insertion component, and in which illumination elements were disposed near the imaging window (see the following Patent Literature 1, for example).

Another conventional intraoral camera comprised a main body case, an intraoral insertion component mounted on the front side of this main body case, an imaging window provided to this intraoral insertion component, and an imaging device that was optically linked to this imaging window and was disposed inside the main body case or inside the intraoral insertion component, and in which illumination elements were disposed near the imaging window. Also, with this conventional intraoral camera, an intraoral lens and an intra-root lens were selectively mounted to the distal end part of the intraoral insertion component depending on whether a tooth was being examined or intra-root imaging was being performed after the treatment of a cavity (see the following Patent Literature 2, for example).

CITATION LIST

Patent Literature

Patent Literature 1: WO 2004-532083
Patent Literature 2: Japanese Laid-Open Patent Application H10-272095

SUMMARY

A problem with the above-mentioned prior publication (Patent Literature 1) was that the intraoral camera could not be used to take a close-up image of a tooth, for example.

Specifically, a conventional configuration merely consisted of disposing illumination elements around the outer periphery of the imaging window. Thus, while the illumination elements were able to illuminate the area below the imaging window, the portion near the imaging window (the imaging object) could not be adequately illuminated. As a result, a good close-up image of the tooth could not be captured.

In view of this, it is an object of the first invention to effectively collect light emitted from the illumination elements on the imaging object, so that the area near a tooth can be properly imaged.

To achieve the stated object, the intraoral camera pertaining to the present invention comprises a main body case, an intraoral insertion component, an imaging window, an imaging device, first and second illumination elements, and a light collecting face. The intraoral insertion component is provided on the distal end side of the main body case and is inserted into the oral cavity of a patient. The imaging window is provided near the distal end of the intraoral insertion component and optically opens with respect to an imaging object within the oral cavity. The imaging device is optically linked to the imaging window and captures an image of the imaging object, and is disposed inside the main body case or inside the intraoral insertion component. The first and second illumination elements are provided on an outer peripheral wall face of the imaging window at the intraoral insertion component, and are disposed opposite each other with the imaging window in between, in a state of being inclined toward the center of the imaging window so that light shines on the imaging object disposed near the imaging window during imaging with the imaging device. The light collecting face is part of the outer peripheral wall face disposed opposite the first and second illumination elements, and is inclined toward the center of the imaging window so as to guide light emitted from the first and second illumination elements to the imaging object disposed near the imaging window during imaging with the imaging device.

Specifically, with the present invention, the first and second illumination elements are disposed at mutually opposing positions with the imaging window in between, on the outer peripheral wall face disposed to the outside of the imaging window at the intraoral insertion component. The first and second illumination elements are attached such that they are inclined toward the center of the imaging window, so as to shine line on the imaging object disposed near the imaging window during imaging with the imaging device. Furthermore, the light collecting face that is part of the outer peripheral wall face disposed opposite the first and second illumination elements is inclined toward the center of the imaging window so as to guide the light emitted from the first and second illumination elements to the imaging object disposed near the imaging window during imaging with the imaging device.

Here, it is necessary to illuminate as close as possible in order to perform close-up imaging within the oral cavity. Accordingly, with the present invention, the illumination elements and the light collecting face are both inclined, which allows the point at which light is collected to be moved closer to the imaging window.

Consequently, when imaging is performed with the imaging device, since the first and second illumination elements are installed at an angle, first the light emitted from the first and second illumination elements goes outside of the imaging window so as to illuminate the imaging object disposed near the imaging window. Then, this light is deflected by the light collecting face, which is part of the outer peripheral wall face, toward the desired point on a vertical line extended from the center of the imaging window toward the outside. As a result, the portion near the outside of the imaging window (that is, the imaging object) can be adequately illuminated. As a result, sufficient brightness can be ensured, and good close-up imaging of a tooth can be performed.

DESCRIPTION OF EMBODIMENTS

The intraoral camera pertaining to an embodiment of the present invention will now be described through reference to FIGS. 1 to 12b.

In this embodiment, the "front and back" direction means the lengthwise direction of the intraoral camera (intraoral insertion component 3, etc.). The side inserted into the oral cavity will be called the "front," and the cord 2 side will be called the "back." In this embodiment, the "up and down" direction means the "up and down" direction in a layout state in which an imaging object (such as a cavity) is directly below the imaging window 3a.

Figure 1:
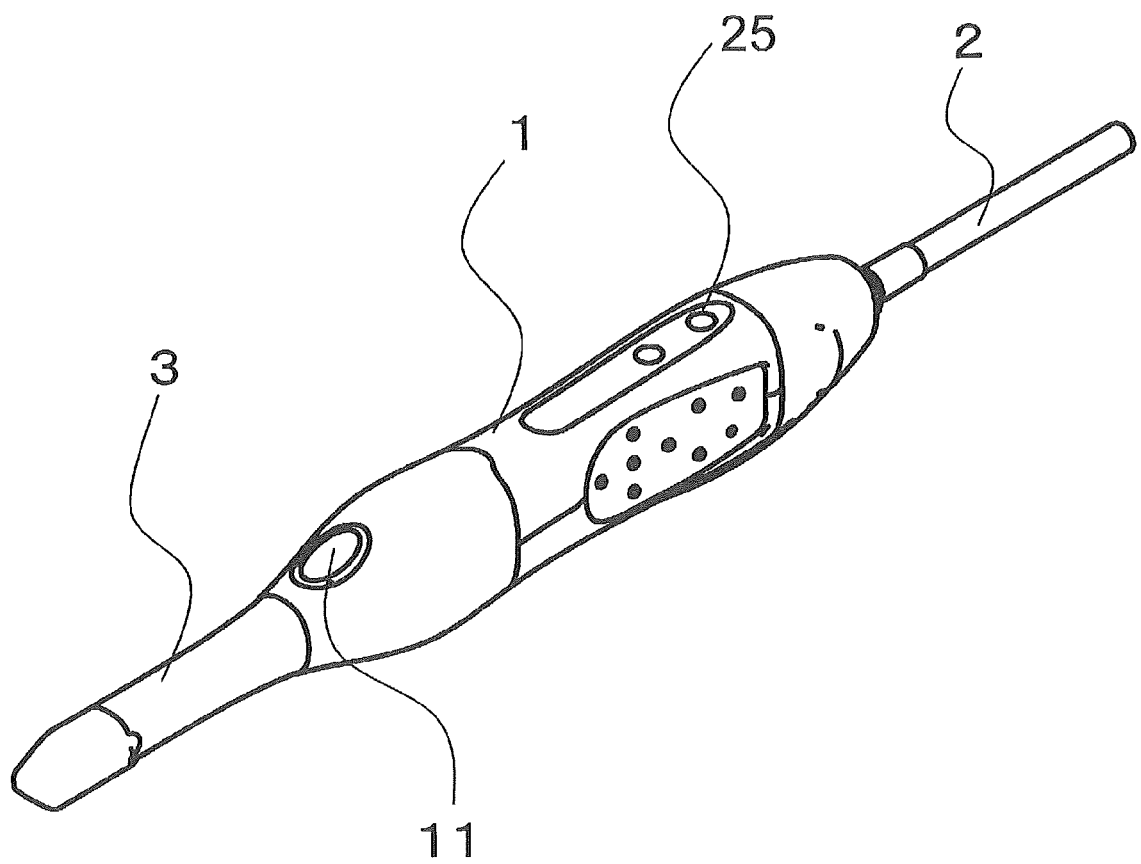
FIG. 1 is an oblique view of the intraoral camera pertaining to an embodiment of the present invention.

In FIG. 1, 1 is a substantially cylindrical main body case. A cord 2 used for power supply and signal communication is connected to the back end side of the main body case 1. Also, an intraoral insertion component 3 is mounted to the distal end side of the main body case 1.

Figure 2:
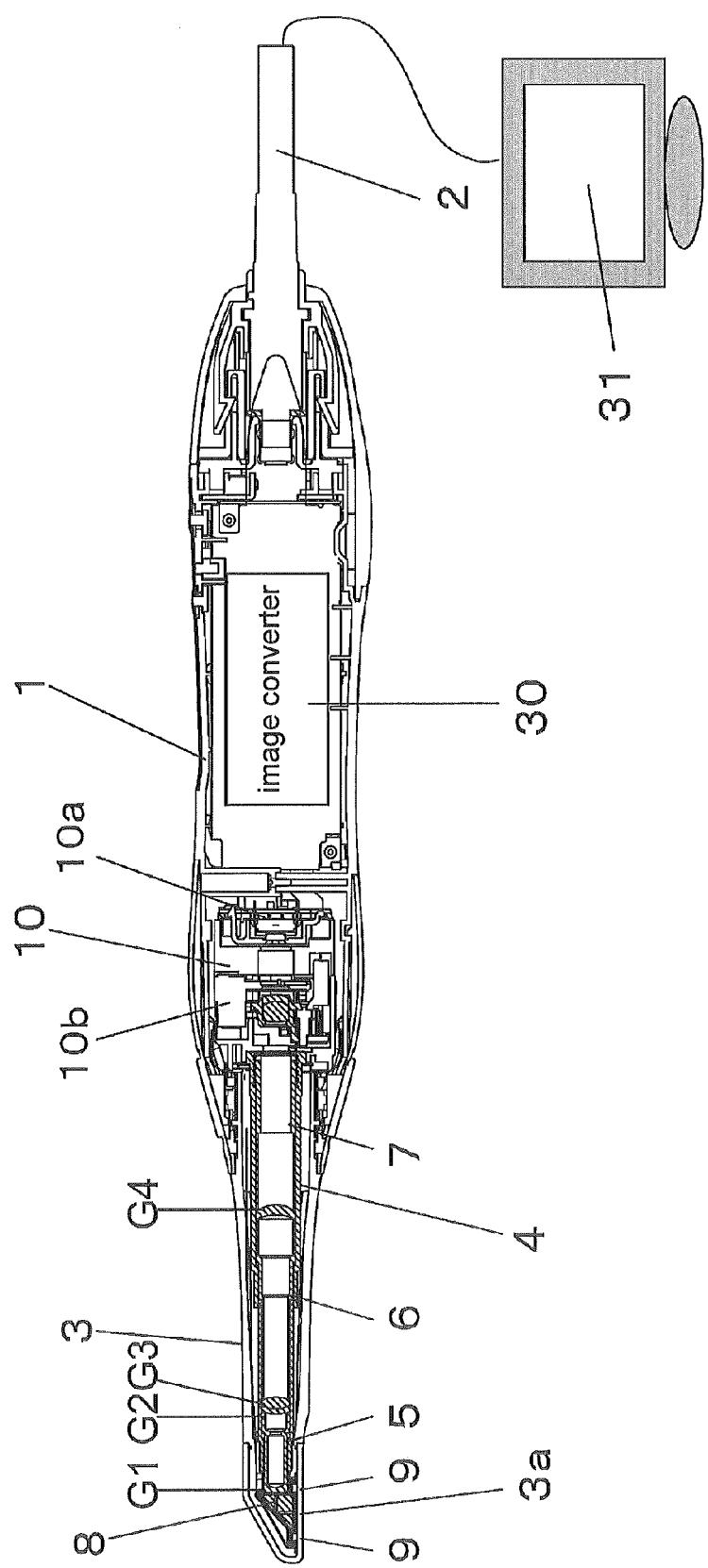
FIG. 2 is a cross section of the intraoral camera in FIG. 1.
Figure 3:
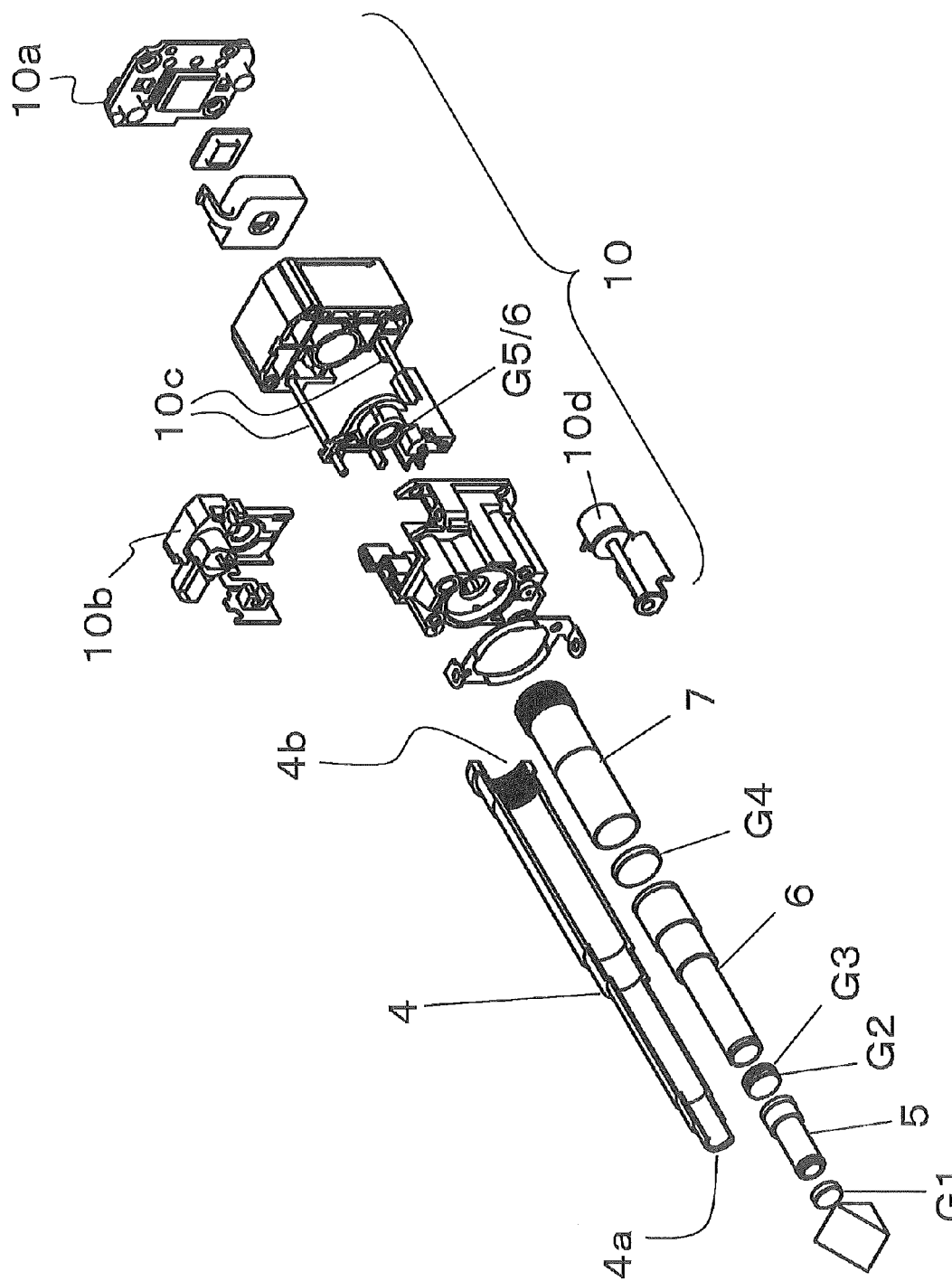
FIG. 3 is an exploded oblique view of the intraoral camera in FIG. 1.

A lens barrel 4 is provided inside the intraoral insertion component 3 as shown in FIGS. 2 and 3.

Figure 4:
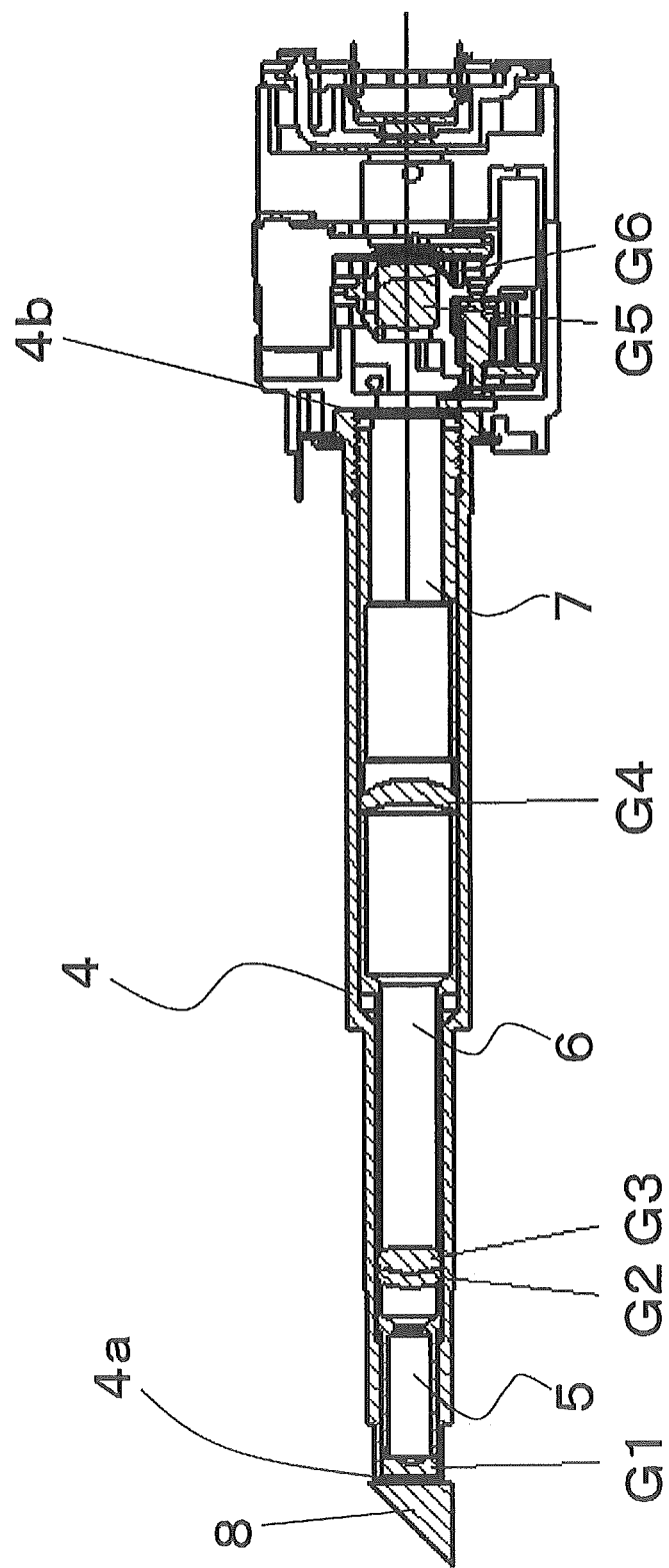
FIG. 4 is a cross section of the lens barrel portion provided to the intraoral camera in FIG. 1.

As shown in FIGS. 3 and 4, the lens barrel 4 has a front opening 4a and a back opening 4b at its two ends, with the opening diameter increasing in stages from the front opening 4a toward the back opening 4b. Also, as shown in FIG. 4, four lens groups G1 to G4, and spacer cylinders 5, 6, and 7 are disposed inside the lens barrel 4.

The four lens groups G1 to G4 and the spacer cylinders 5, 6, and 7 will now be described in the order in which they are installed in the lens barrel 4.

First, the lens group G1 (the first group) is inserted through the back opening 4b of the lens barrel 4, and as shown in FIG. 4 is pushed in to the position of the front opening 4a of the lens barrel 4. The lens group G1 is positioned by having the outer periphery of the lens group G1 at this position come into contact with the inner peripheral face of the lens barrel 4.

Then, the spacer cylinder 5 is pushed in through the back opening 4b of the lens barrel 4 to the lens group G1. The spacer cylinder 5 is positioned in this state.

Next, the lens groups G2 and G3 (second and third groups) are put in through the back opening 4b of the lens barrel 4, and are pushed to the spacer cylinder 5 as shown in FIG. 4. The lens groups G2 and G3 are positioned in this state.

Next, the spacer cylinder 6 is pushed in through the back opening 4b of the lens barrel 4 to a position where it hits the lens group G3. The spacer cylinder 6 is positioned in this state.

Next, the lens group G4 (fourth group) is put in through the back opening 4b of the lens barrel 4, and is pushed in to a position where it hits the back end of the spacer cylinder 6, as shown in FIG. 4. The lens group G4 is positioned in this state.

Finally, the spacer cylinder 7 is pushed in through the back opening 4b of the lens barrel 4 until it hits the lens group G4. The spacer cylinder 7 is positioned in this state.

The front opening 4a in the lens barrel 4 is optically linked to an imaging window 3a provided to the lower face portion of the intraoral insertion component 3 opposite the imaging object. A reflecting element 8 (an object with a triangular cross sectional shape when viewed from the front as in FIG. 2 is also called a prism), which is used as an example of a light guide element, is provided between this imaging window 3a and the front opening 4a of the lens barrel 4.

Figure 5:
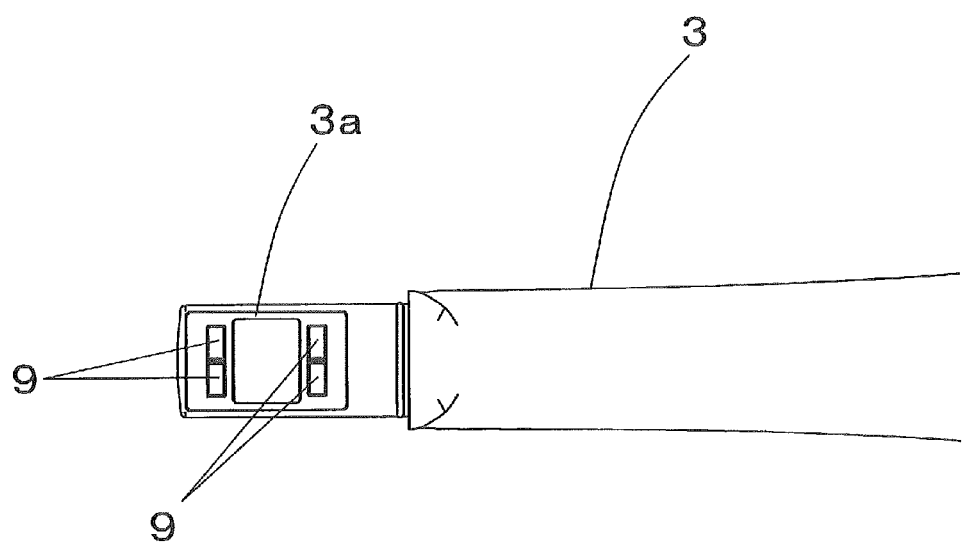
FIG. 5 is a bottom view of the intraoral insertion component provided to the intraoral camera in FIG. 1.

Also, as shown in FIG. 5, the imaging window 3a is formed as a square open portion. Two (a total of four) illumination elements (first and second illumination elements) 9 are disposed on the outside of each of the two opposing sides of the square in the lengthwise direction of the intraoral insertion component 3.

Meanwhile, as shown in FIG. 3, an imaging device 10 is optically linked to the back opening 4b of the lens barrel 4.

In the above configuration, if, for example, an image of inside the oral cavity is acquired by using an intraoral camera for caries treatment or the like, a vinyl cover (not shown) is mounted to the outer periphery of the intraoral insertion component 3 shown in FIG. 1 and inserted into the oral cavity in this state, and illumination of the tooth that is the imaging object is performed by the illumination elements 9 in this state. At this point, video (optical information) obtained from the imaging window 3a is sent to the imaging device 10 via the reflecting element 8, the lens groups G1, G2, G3, and G4, and fifth and sixth lens groups G5 and G6 (see FIG. 4) provided outside the lens barrel 4. After this, the video (optical information) is displayed on a monitor (not shown) via the cord 2.

Here, when the dentist has found the tooth to be imaged while looking at the monitor, he presses an imaging button 11 (shown in FIG. 1) to record that image as a still picture to a memory (not shown) in the monitor.

In this embodiment, the illumination elements 9 are disposed near the imaging window 3a that is disposed opposite the tooth that is the imaging object. Consequently, the illumination elements 9 are disposed near the tooth that is the imaging object, so even if the illumination of the illumination elements 9 is raised, a sufficiently clear image can still be acquired by the imaging device 10. Thus, the illumination elements 9 consume less power, and as a result the problem wherein the temperature of the tooth that is the imaging object rises abnormally can be avoided.

Also, in this embodiment, the front opening 4a of the lens barrel 4 is disposed near this imaging window 3a portion, and the lens barrel 4 is made of metal. Accordingly, any heat generated near this imaging window 3a is effectively transferred from the front opening 4a of the lens barrel 4 to the back opening 4b, which minimizes the increase in temperature near the imaging window 3a.

In other words, even when the area near the imaging window 3a touches the skin or teeth inside the oral cavity during imaging inside the oral cavity, the patient will not feel any uncomfortable heat, and the imaging work can be carried out more pleasantly.

Also, since the lens barrel 4 is formed from metal, it can be worked more precisely than if it were formed from plastic or the like. Thus, the lens groups G1 to G4 can be properly disposed at the specified locations in the lens barrel 4.

Furthermore, in this embodiment, the spacer cylinders 5, 6, and 7 are formed from a metal that can be precisely worked, in order to properly dispose the lens groups G1 to G4. Also, black films are provided on at least the inner face side of the spacer cylinders 5, 6, and 7. This prevents the unnecessary reflection of light on the inner faces of the spacer cylinders 5, 6, and 7.

The basic constitution, action, and effect in this embodiment will be understood from the above description, and the main features of the intraoral camera pertaining to this embodiment will now be described.

As discussed above, in this embodiment, in order to obtain sufficient illumination when imaging inside the oral cavity, the illumination elements 9 are disposed near the imaging window 3a, and the configuration is such that the portion near the imaging window 3a (on the imaging object side) can also be fully illuminated. This configuration and its features will now be described.

Figure 6:
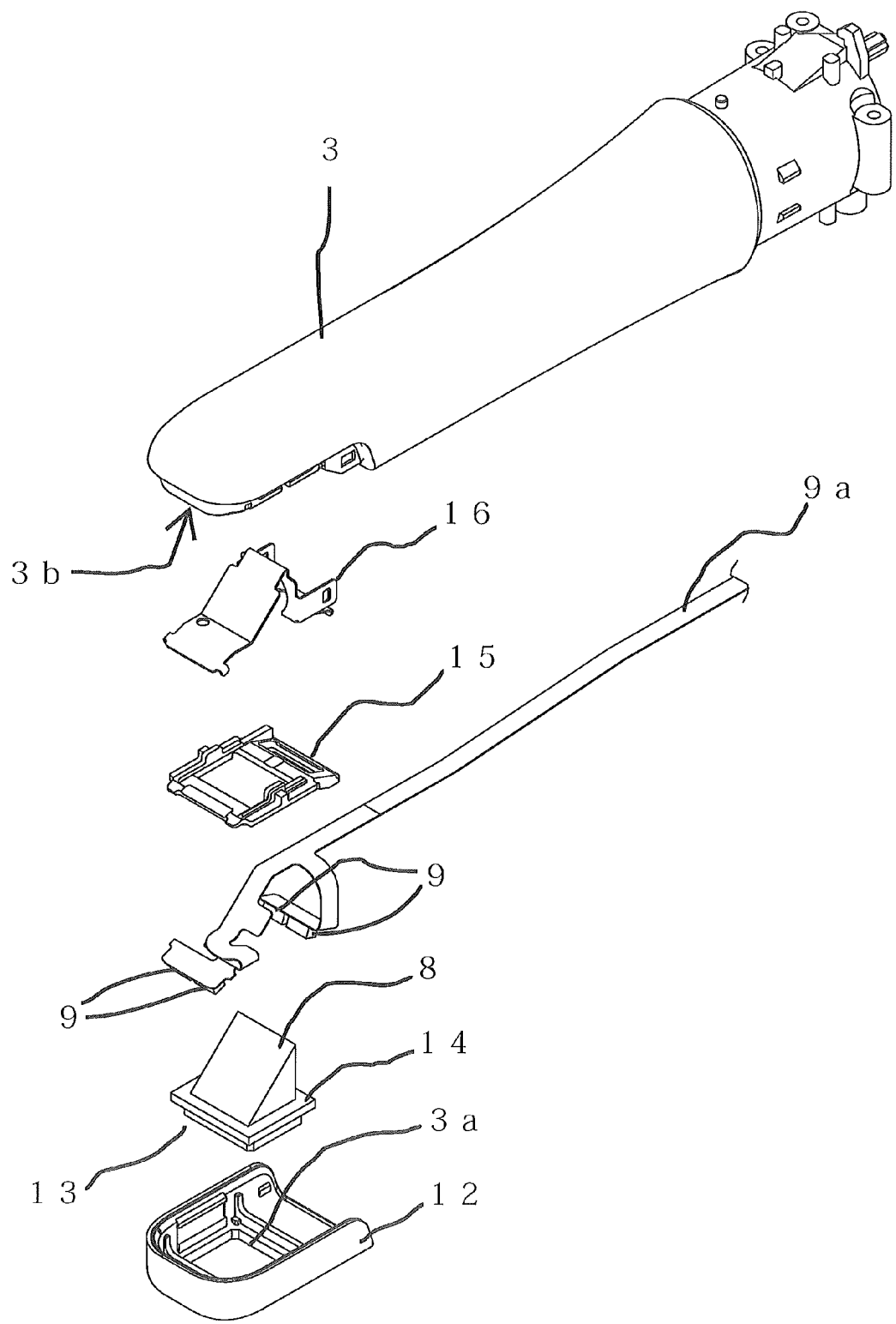
FIG. 6 is an exploded oblique view of the intraoral insertion component in FIG. 5.

FIG. 6 is an exploded oblique view of the intraoral insertion component 3.

As shown in FIG. 6, an imaging window structure 12 is attached on the lower face side at the distal end of the intraoral insertion component 3. The imaging window structure 12 is formed integrally with the imaging window 3a and light collecting faces 17a and 17b (discussed below). A light guide element 13 is disposed at a position of the intraoral insertion component 3 that is opposite the imaging window 3a.

The light guide element 13 has the reflecting element 8, which reflects optical information obtained from the imaging window 3a to the main body case 1 side, and a cover element 14, which allows the reflecting element 8 to be mounted inside the imaging window 3a on the lower face side of the reflecting element 8.

The size of the bottom face of the cover element 14 in the lengthwise direction of the intraoral insertion component 3 is somewhat smaller than the size of the open portion of the imaging window 3a, and the size of the bottom face of the reflecting element 8 is smaller than the size of the imaging window 3a. The size of the bottom face of the cover element 14 in the lengthwise direction of the intraoral insertion component 3 is also larger than the size of the bottom face of the reflecting element 8.

Consequently, when the reflecting element 8 is attached to the imaging window structure 12 via the cover element 14, this allows the light guide element 13 to be mounted to the imaging window structure 12 in a state in which the cover element 14 has been fitted to the open portion of the imaging window 3a.

The configuration of the illumination elements 9 will now be described.

The four illumination elements 9 are mounted to a flexible conductive substrate 9a and are electrically connected to the main body case 1 side. The flexible conductive substrate 9a is mounted on its distal end side to an illumination element holder 15. The illumination element holder 15 is mounted to the intraoral insertion component 3 via a linking member 16 that is linked to an open portion 3b provided at the distal end of the intraoral insertion component 3.

Specifically, the imaging window structure 12 to which the light guide element 13 is mounted is fitted into the open portion 3b formed at the distal end of the intraoral insertion component 3 in a state of being sandwiched between the illumination element holder 15 and the illumination elements 9 mounted to the intraoral insertion component 3, as discussed above.

The layout relation between the illumination elements 9 and the imaging window structure 12, and the shape of the imaging window structure 12 in the above configuration will be described in detail below.

Figure 7:
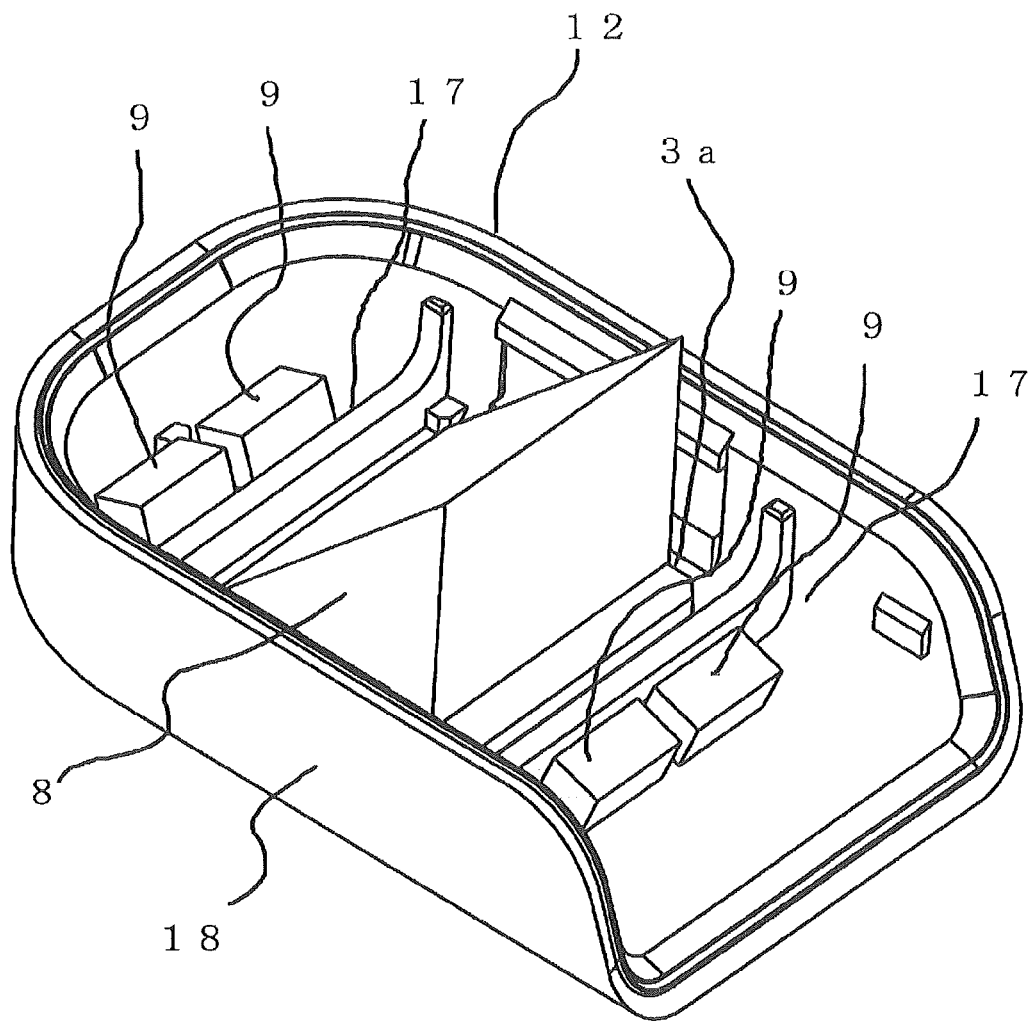
FIG. 7 is an exploded oblique view of the main components of the intraoral insertion component in FIG. 5.

First, the layout relation between the illumination elements 9 and the imaging window structure 12 will be described through reference to FIGS. 7, 8, and 9. In FIG. 7, the illumination element holder 15, the linking member 16, and the flexible conductive substrate 9a are not depicted in order to facilitate an understanding of the layout relation between these components.

As shown in FIG. 7, the imaging window structure 12 has an outer peripheral wall face 17 provided to the bottom face on the inside of the periphery of the imaging window 3a (the side mounted to the intraoral insertion component 3). The illumination elements 9 are disposed to the outside of the two sides of the substantially square imaging window 3a that are opposite each other in the lengthwise direction of the intraoral insertion component 3, on the bottom face of the outer peripheral wall face 17.

Figure 8:
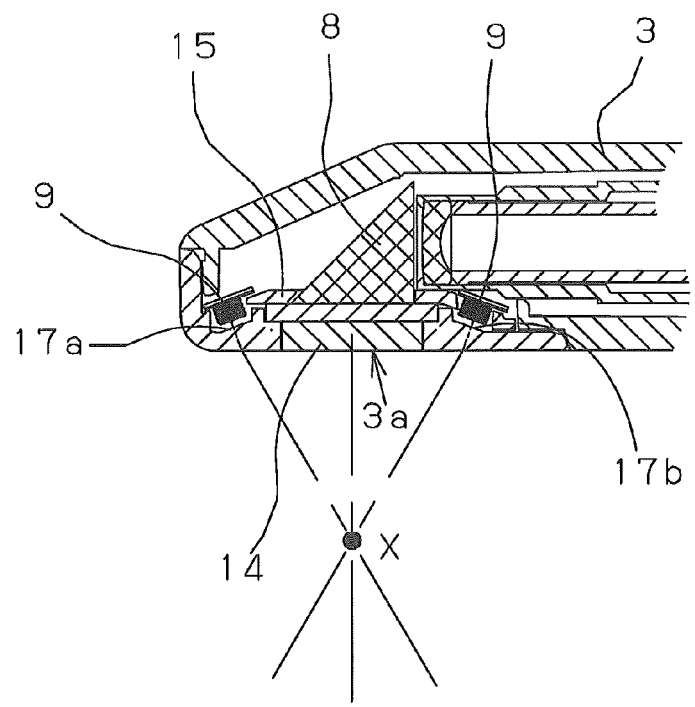
FIG. 8 is a cross section of the intraoral insertion component in FIG. 5.

FIG. 8 is a cross section of the intraoral insertion component 3 as seen from a side face.

As shown in FIG. 8, the illumination elements 9 are disposed at positions to the outside of the imaging window 3a within the intraoral insertion component 3, and inclined so as to shine light toward a point X on a vertical line extending from the center of the imaging window 3a toward the imaging object side (the lower side in FIG. 8).

Also, portions of the outer peripheral wall face 17 that are opposite the illumination elements 9 (the light collecting faces 17a and 17b) are formed inclined so as to guide the light toward the point X on the vertical line extending from the center of the imaging window 3a toward the imaging object side (the lower side in FIG. 8). Consequently, part of the outer peripheral wall face 17 can be utilized as the light collecting faces 17a and 17b that collect the light emitted from the illumination elements 9 at the above-mentioned point X. Also, utilizing these light collecting faces allows the light to be effectively deflected and directed as close as possible to the imaging window 3a.

The light collecting faces 17a and 17b and the attachment faces of the above-mentioned illumination elements 9 are formed so as to be substantially parallel. This results in the above-mentioned inclined faces being substantially parallel, so light is deflected by a so-called prism effect, in which incident light that is perpendicular to the inclined faces moves straight ahead, while at the outer emission faces the light is bent closer. As to the angular relation between the inclined faces, if the angle is too small, the point X at which the light is collected is too far away from the imaging window 3a, but if the angle is too large, the focal distance from the device will be too long and there will not be enough space, objects will get in the way, and other such problems will be encountered. Therefore, in this embodiment, the inclination angle is set to be approximately 20 degrees with respect to the horizontal direction. However, the inclination angle is not limited to this, and can be varied as needed.

Also, since the light collecting faces 17a and 17b and the attachment faces of the illumination elements 9 are both inclined with respect to the horizontal direction as in this embodiment, light can be collected at a location closer to the imaging window 3a.

Figure 9:
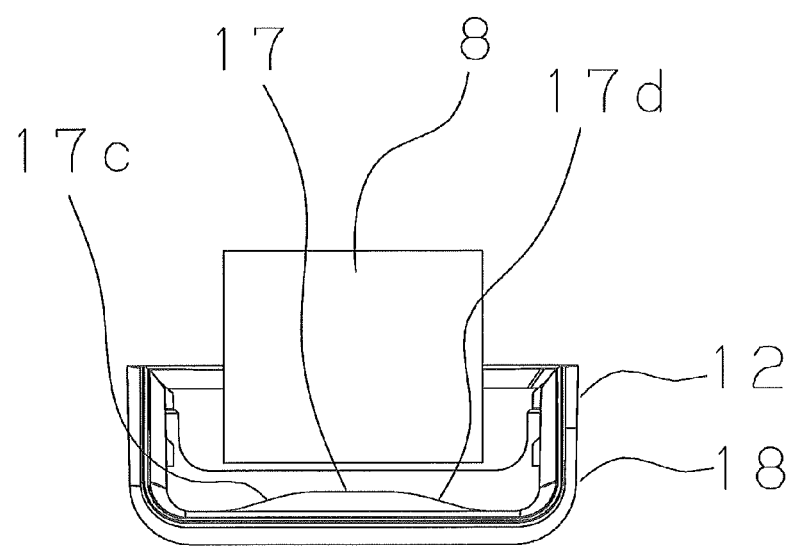
FIG. 9 is a front view of the main components of the intraoral insertion component in FIG. 5 as seen from the rear.

FIG. 9 is a front view of the intraoral insertion component 3 (the imaging window structure 12, etc.) as seen from the back (the main body case 1 side).

In FIG. 9, the illumination elements 9 is not depicted in order to make it easy to understand the shape of the imaging window structure 12.

As discussed above, the outer peripheral wall face 17 of the imaging window structure 12 is formed as shown in FIG. 8, with its light collecting faces 17a and 17b inclined to the inside with respect to the horizontal plane in FIG. 8, so that light is guided toward the point X (the lower side in FIG. 8) on the vertical line extending from the center of the imaging window 3a as seen from the side.

Furthermore, in this embodiment, when the imaging window structure 12 is viewed from the back, light collecting faces 17c and 17d (the two ends of the light collecting component) that are part of the outer peripheral wall face 17 are formed so as to be inclined to the inside with respect to the horizontal plane in FIG. 9, just as are the light collecting faces 17a and 17b. Although not shown in the drawings, the light collecting faces have the same shape in the lengthwise direction of the intraoral insertion component 3 in the imaging window structure 12.

With the intraoral camera of this embodiment, because of the above configuration, light emitted from the illumination elements 9 is first directed at the point X on the outside of the imaging window 3a (below the imaging window 3a in FIG. 8) within the intraoral insertion component 3. Then, this light is defected by the light collecting faces 17a and 17b and the light collecting faces 17c and 17d of the outer peripheral wall face 17 toward the point X on the outside of the imaging window 3a.

The light collecting faces 17c and 17d shown in FIG. 9, which is a cross section perpendicular to FIG. 8, have the action of deflecting and collecting illumination light. That is, the light collecting faces 17a, 17b, 17c, and 17d have a deflecting action for shining light on a position that is closer to the imaging window 3a. These light collecting faces (inclined faces) 17a to 17d do not deflect light that is incident perpendicularly, but do inwardly deflect light that incident from the outer peripheral wall face.

Consequently, the portion close to the imaging window 3a on the outside of the imaging window 3a (below the imaging window 3a in FIG. 8), that is, the imaging object, can be sufficiently illuminated. As a result, close-up imaging of a tooth can be properly performed with an intraoral camera in a state in which adequate brightness is ensured.

With this embodiment, furthermore, the outer peripheral wall face 17 that is part of the imaging window structure 12 is a transparent face formed from a transparent material, and an outer wall face 18, which is farther to the outside than the outer peripheral wall face 17, but is similarly a part of the imaging window structure 12, is an opaque face or a reflective face formed from an opaque material or from a material that reflects.

Consequently, light emitted from the illumination elements 9 can be collected at the outer peripheral wall face 17 (serving as the light collecting face) without leaking outside of the intraoral insertion component 3 through the portion of the outer wall face 18. As a result, compared to when the outer wall face 18 is formed from a transparent material, the portion of the imaging window 3a closer to the outside (the imaging object) can be sufficiently illuminated more efficiently.

Intra-root imaging performed with the above-mentioned intraoral camera will now be described through reference to FIGS. 1 to 4, FIG. 10 and FIG. 11.

As discussed above, in the above embodiment close-up imaging of a tooth can be performed in a state in which adequate brightness is ensured by actively collecting the light from the four illumination elements 9 at the point X on the vertical line extending from the center of the imaging window 3a. In this embodiment, in addition to the configuration discussed above, a mode setting switch 25 for switching between close-up imaging mode and intra-root imaging mode and the like are provided to further enhance the effect.

Specifically, in the close-up imaging of a tooth as discussed above, when a cavity is found, if that cavity has progressed to a serious state, the following measures must be taken. Specifically, as shown in FIG. 10, a treatment hole 22 that goes through the enamel 20 and dentin 21 of a tooth 19 is formed by a dentist using a dental instrument (not shown), after which a reamer (not shown) is inserted through this treatment hole 22, and the dental nerve 23 is extracted.

At this point, since the dental nerve 23 is inside the pulp chamber 24, all of it must be extracted. In dental treatment, it must be confirmed whether or not the dental nerve 23 has been completely extracted from inside the pulp chamber 24.

Figure 10:
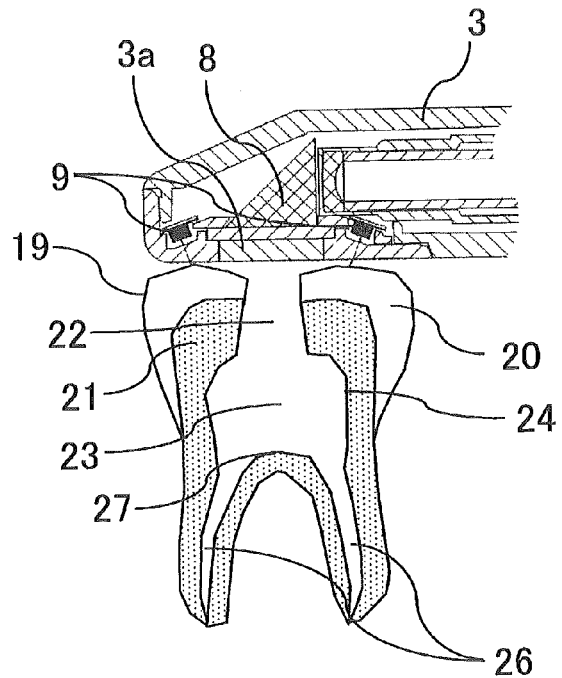
FIG. 10 is a diagram of the state when intra-root imaging is performed using the intraoral camera in FIG. 1.

In this embodiment, as shown in FIG. 10, a portion of the imaging window 3a of the intraoral insertion component 3 of the above-mentioned intraoral camera is disposed above the treatment hole 22, and it is confirmed in this state whether or not the dental nerve 23 has been completely extracted.

At this point, if the dentist operates the mode setting switch 25 shown in FIG. 1, the intraoral camera is switched from the close-up imaging mode to the intra-root imaging mode. When the intra-root imaging mode is set, the fifth and sixth lens groups G5 and G6 of the imaging device 10 shown in FIG. 4 move along two guide poles 10c under the drive force of the motor (movement mechanism) 10d shown in FIG. 3, to a position that is closer to an imaging element 10a than in the above-mentioned close-up imaging mode.

As shown in FIG. 3, the above-mentioned motor 10d and two guide poles 10c can be used as the movement mechanism that moves the lens groups G5 and G6.

As a result, the imaging focal position of the imaging device 10 is changed to a position 7 mm below (inside the root) from the top face of the tooth 19. The 7 mm here refers to the distance from the upper face of the tooth 19 shown in FIG. 10 to a branching point 27 of a root canal 26, when the patient is a typical adult.

Furthermore, in this embodiment, when the above-mentioned mode setting switch 25 is operated to switch from the close-up imaging mode to the intra-root imaging mode, the aperture of an iris unit 10b shown in FIGS. 2 and 3 is opened by about one stage more than in the close-up imaging mode. Consequently, in the intra-root imaging mode, it is easier to bring in light than in the close-up imaging mode, and the light required to perform intra-root imaging mode can be adequately brought in.

Also, in this embodiment, a mechanism that adjusts the aperture by sliding iris vanes 28 and 29 up and down as shown in FIGS. 12a and 12b is employed as the adjustment mechanism for the aperture of this iris unit 10b.

As a result, in the intra-root imaging mode, the amount of light that reaches the imaging element 10a is increased, and a brighter image of the treatment hole 22 can be captured.

Furthermore, in this embodiment, when the mode setting switch 25 is operated to switch from the close-up imaging mode to the intra-root imaging mode, the following processing is performed on the image captured by the imaging element 10a.

Specifically, with the intraoral camera of this embodiment, the image captured within the root is enlarged for display on a display 31 (see FIG. 2) more than in the above-mentioned close-up imaging mode, by an image converter (see FIG. 2) connected to the imaging element 10a.

As a result, the root canal 26 portion within the pulp chamber 24 can be better enlarged and highlighted in the resulting captured image, so it can be easily confirmed whether or not the dental nerve 23 has been completely extracted from the pulp chamber 24.

Figure 11:
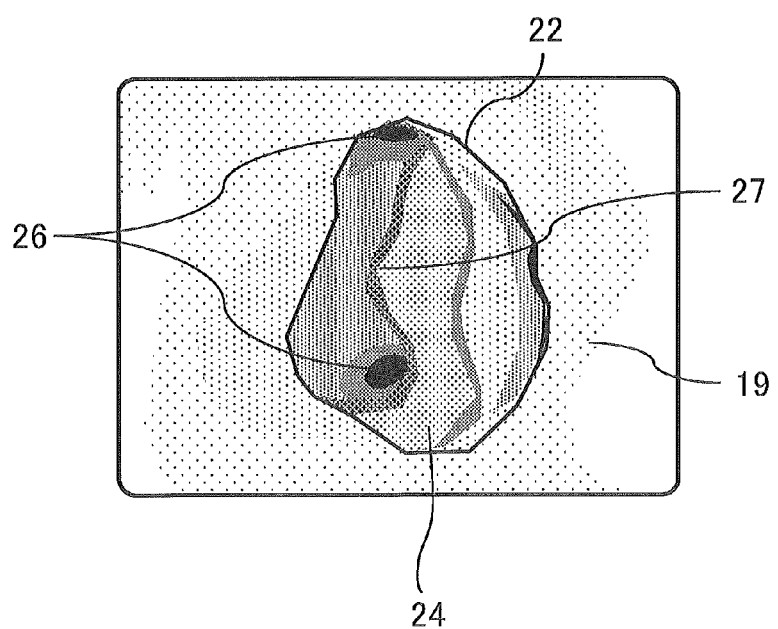
FIG. 11 is a diagram of an image obtained by the intra-root imaging in FIG. 10.
Figure 12:
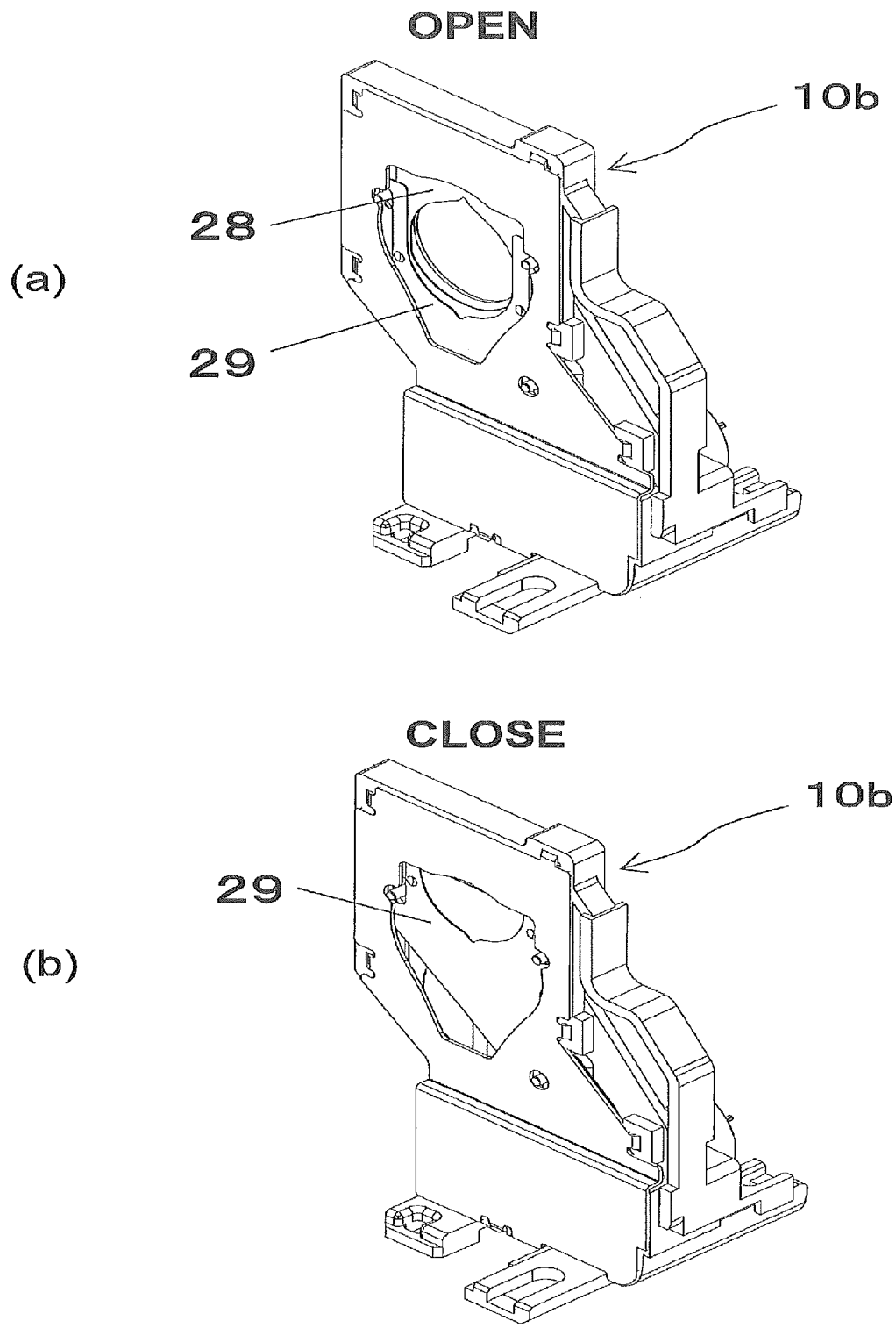
FIGS. 12a and 12b are diagrams of the aperture adjusting mechanism in the intraoral camera in FIG. 1.

FIG. 11 is an image of inside the root captured as above.

As shown in FIG. 11, the root canal 26 can be clearly seen on both sides of the branching point 27, and it can be seen that the dental nerve 23 that was inside the pulp chamber 24 has been neatly extracted.

Thus, obtaining a clear captured image is also greatly affected by actively collecting the light from the above-mentioned four illumination elements 9 at the center of the imaging window 3a.

Specifically, if light is thus actively collected by the illumination elements 9 from the upper four sides of the tooth 19, this light will go into the tooth 19 and reach the root canal 26 portion, with this tooth 19 itself acting as a light conductor. Thus, the inside of the root can be adequately illuminated, so if the focal position of the imaging device 10 is set at the desired position in the root, a clear captured image such as that in FIG. 11 can be obtained.

Therefore, with this embodiment, when performing close-up imaging and intra-root imaging of the tooth 19, an extremely high-quality image can be captured, and the imaging mode can be switched by a simple operation entailing only the operation of the mode setting switch 25. As a result, there is no need to replace a lens, etc., in order to change the imaging focal distance according to the imaging mode, so the dental work involving close-up imaging and intra-root imaging can be carried out much more easily than in the past.

In this embodiment, an example was given in which the close-up imaging mode was switched to the intra-root imaging mode when the mode setting switch 25 was pressed, but the switching of the imaging modes may be accomplished by pressing a single switch, or may be accomplished by pressing a switch provided for each mode.

INDUSTRIAL APPLICABILITY

As discussed above, the first invention is expected to find wide application as an intraoral camera because it has the effect of allowing close-up imaging of a tooth to be carried out favorably.

As discussed above, the second invention is expected to find wide application as an intraoral camera because close-up imaging of a tooth can be carried out favorably, and because intra-root imaging can be performed without having to change the lens as in the past, so the work is much easier than in the past.

REFERENCE SIGNS LIST main body case
2 cord
3 intraoral insertion component
3a imaging window
3b open portion
4 lens barrel
4a front opening
4b back opening
5 spacer cylinder
6 spacer cylinder
7 spacer cylinder
8 reflecting element
9 illumination element (first and second illumination elements)
9a flexible conductive substrate
10 imaging device
10a imaging element
10b iris unit
10c guide pole
10d motor
11 imaging button
12 imaging window structure
13 light guide element
14 cover element
15 illumination element holder
16 linking member
17 outer peripheral wall face
17a, 17b light collecting face (light collecting faces)
17c, 17d light collecting face (ends of light collecting component)
18 outer peripheral wall face
19 tooth
20 enamel
21 dentin
22 treatment hole
23 dental nerve
24 pulp chamber
25 mode setting switch
26 root canal
27 branching point
28 iris vane
29 iris vane
30 image converter
31 motor
G1 lens group
G2 lens group
G3 lens group
G4 lens group
G5 lens group
G6 lens group

The invention claimed is:

1. An intraoral camera, comprising:
a main body case;
an intraoral insertion component that is provided on the distal end side of the main body case and is inserted into the oral cavity of a patient;
an imaging window that is provided near the distal end of the intraoral insertion component and optically opens with respect to an imaging object within the oral cavity;
an imaging device that is optically linked to the imaging window and captures an image of the imaging object, and that is disposed inside the main body case or inside the intraoral insertion component;
first and second illumination elements that are provided on an outer peripheral wall face of the imaging window at the intraoral insertion component, and are disposed opposite each other with the imaging window in between, in a state of being inclined toward the center of the imaging window so that light shines on the imaging object disposed near the imaging window during imaging with the imaging device; and
first and second light collecting faces that are part of the outer peripheral wall face, and that are disposed in front of the first and second illumination elements, respectively, and that are inclined toward the center of the imaging window so as to guide light emitted from the first and second illumination elements through the first and second light collecting faces, respectively, to the imaging object disposed near the imaging window during imaging with the imaging device, wherein the first and second light collecting faces deflect some of the light by a prism effect such that light that is perpendicular to the faces moves straight through, while other light is bent closer to the imaging window.

2. The intraoral camera according to claim 1, wherein the outer peripheral wall face of the intraoral insertion component is a transparent face, and a side wall disposed more to the outside than the outer peripheral wall face when viewed from the imaging window is an opaque face or a reflective face.

3. The intraoral camera according to claim 1,
wherein the intraoral insertion component has an imaging window structure that is disposed at the distal end side of the intraoral insertion component, and in which the imaging window is formed, and
the imaging window structure is formed so that the imaging window and the first and second light collecting faces are integrated.

4. The intraoral camera according to claim 1,
wherein the imaging window is formed in a substantially quadrangular shape, and
the illumination elements are formed at positions on the outside of two opposite sides of the substantially quadrangular shape.

5. The intraoral camera according to claim 1,
wherein the outer peripheral wall face has first and second light collecting components that include the first and second light collecting faces, respectively, at the outer peripheral portion of the imaging window, and
the first and second light collecting components are inclined toward the center of the imaging window.

6. The intraoral camera according to claim 1,
further comprising a light guide element that is disposed at a position opposite the imaging window in the intraoral insertion component, and is optically linked to the imaging device.

7. The intraoral camera according to claim 6,
wherein the light guide element has a reflecting element that guides optical information from the imaging window to the main body case side, and a cover element that is disposed on a face of the reflecting element opposite the imaging window and that is attached to the imaging window.

8. The intraoral camera according to claim 7,
wherein the size of the cover element in the lengthwise direction of the intraoral insertion component is greater than the size in the lengthwise direction of the reflecting element.

9. The intraoral camera according to claim 1,
further comprising a mode setting switch configured to switch the imaging device between a close-up imaging mode and an intra-root imaging mode.

10. The intraoral camera according to claim 9,
wherein the imaging device in the intra-root imaging mode sets imaging focal position to a position that is farther than that in the close-up imaging mode.

11. The intraoral camera according to claim 10,
wherein the imaging device has a plurality of fixed imaging focal positions, and these imaging focal positions are used selectively according to the close-up imaging mode and the intra-root imaging mode.

12. The intraoral camera according to claim 9,
wherein the imaging device in intra-root imaging mode sets the aperture of the imaging device to a position that is more open than that in the close-up imaging mode.

13. The intraoral camera according to claim 9,
wherein the imaging device in intra-root imaging mode displays an image captured by the imaging device in a larger size than that in the close-up imaging mode.

* * * * *